US009511365B2

(12) United States Patent
Mazumdar et al.

(10) Patent No.: US 9,511,365 B2
(45) Date of Patent: *Dec. 6, 2016

(54) SENSOR HOUSING AND REAGENT CHEMISTRY

(71) Applicant: ANDalyze, Inc., Champaign, IL (US)

(72) Inventors: Debapriya Mazumdar, Chicago, IL (US); David G. Kellner, Urbana, IL (US)

(73) Assignee: ANDalyze, Inc., Champaign, IL (US)

( * ) Notice: Subject to any disclaimer, the term of this patent is extended or adjusted under 35 U.S.C. 154(b) by 28 days.

This patent is subject to a terminal disclaimer.

(21) Appl. No.: 14/333,168

(22) Filed: Jul. 16, 2014

(65) Prior Publication Data

US 2014/0329235 A1 Nov. 6, 2014

Related U.S. Application Data

(63) Continuation of application No. 12/838,762, filed on Jul. 19, 2010, now Pat. No. 8,815,156.

(51) Int. Cl.
| | |
|---|---|
| *G01N 15/06* | (2006.01) |
| *B01L 3/00* | (2006.01) |
| *G01N 21/64* | (2006.01) |
| *C12Q 1/68* | (2006.01) |
| *G01N 33/20* | (2006.01) |

(52) U.S. Cl.
CPC .............. *B01L 3/5023* (2013.01); *B01L 3/502* (2013.01); *C12Q 1/68* (2013.01); *G01N 21/645* (2013.01); *G01N 33/20* (2013.01)

(58) Field of Classification Search
None
See application file for complete search history.

(56) References Cited

U.S. PATENT DOCUMENTS

| | | | | |
|---|---|---|---|---|
| 3,682,321 A | * | 8/1972 | Smith | B01D 23/28 210/477 |
| 2005/0282186 A1 | * | 12/2005 | Lu | C12Q 1/68 435/20 |
| 2011/0008909 A1 | * | 1/2011 | Homrig | B01L 3/5023 436/501 |

FOREIGN PATENT DOCUMENTS

| | | | | |
|---|---|---|---|---|
| EP | 0364173 | * | 4/1990 | ............ B01D 29/01 |

OTHER PUBLICATIONS

Gray, B.L. et al. Interlocking mechanical and fluidic interconnections for microfluidic circuit boards, 2004, Sensors and Actuators A, vol. 112, pp. 18-24.*

* cited by examiner

*Primary Examiner* — Robert Xu
(74) *Attorney, Agent, or Firm* — Nancy R. Gamburd; Gamburd Law Group LLC

(57) ABSTRACT

A sensor comprises a sensor housing, having a channel; a porous substrate, in the channel; an analysis chemistry reagent, on the porous substrate; and a nozzle, in fluid connection with the channel. The porous substrate fills a cross section of the channel, and the cross-sectional area of the channel at the porous substrate is greater than the cross-sectional area at the nozzle.

17 Claims, 9 Drawing Sheets

SENSOR HOUSING AND REAGENT CHEMISTRY

CROSS-REFERENCE TO A RELATED APPLICATION

This application is a continuation of and claims priority to and the benefit of U.S. patent application Ser. No. 12/838,762, filed Jul. 19, 2010, inventors Debapriya Mazumdar et al., titled "Sensor Housing and Reagent Chemistry", which is commonly assigned herewith, the entire contents of which are incorporated herein by reference with the same full force and effect as if set forth in their entirety herein, and with priority claimed for all commonly disclosed subject matter.

BACKGROUND

Methods which permit real time detection of $Pb^{2+}$ and other metal ions are very important in the fields of environmental monitoring, clinical toxicology, wastewater treatment, and industrial process monitoring and can lead to preventative measures or lower risks associated with metal contaminants. However, traditional methods of detecting metal ions are cumbersome, often requiring samples collected in the field to be brought back and analyzed in a laboratory setting. Methods are needed for real time detection and monitoring of metal ions in industrial and biological systems.

Fluorescence spectroscopy is a technique well suited for detection of very small concentrations of analytes. Fluorescence provides significant signal amplification, since a single fluorophore can absorb and emit many photons, leading to strong signals even at very low concentrations. In addition, the fluorescence time-scale is fast enough to allow real-time monitoring of concentration fluctuations. Fluorescent properties only respond to changes related to the fluorophore, and therefore can be highly selective. Also, fluorometers, for measuring fluorescence signals, are commercially available.

SUMMARY

In a first aspect, the present invention is a sensor, comprising a sensor housing, having a channel; a porous substrate, in the channel; an analysis chemistry reagent, on the porous substrate; and a nozzle, in fluid connection with the channel. The porous substrate fills a cross section of the channel, and the cross-sectional area of the channel at the porous substrate is greater than the cross-sectional area at the nozzle.

In a second aspect, the present invention is a kit, comprising a box; and a plurality of sensors, and a plurality of cuvettes. One of the plurality of sensors and one of the plurality of cuvettes are each in a first sealed bag of a plurality of first sealed bags.

In a third aspect, the present invention is a method of detecting an ion, comprising flowing a sample fluid through the channel of a sensor, to produce a product; collecting the product; and detecting the presence of the product.

The following definitions are included to provide a clear and consistent understanding of the specification and claims.

The term "sample" is defined as a composition suspected of containing the analyte of interest that will be subjected to analysis. Typically, a sample for analysis is in liquid form, or can be converted into liquid form, and preferably the sample is an aqueous composition. A sample may be from any source, such as an industrial sample from a waste stream, or a biological sample such as blood, urine or saliva. Other examples include drinking water, paint, or paint chips. A sample may be treated, such as by extract, dilution or filtration, or it may be a reconstituted precipitate from an industrial or biological source.

The term "analyte" is defined as one or more substances potentially present in a sample, for which the analysis tests. An analysis for an analyte determines the presence, quantity or concentration, of the analyte in the sample.

The term "analysis chemistry reagents" refers to one or more reagents, that when reacted with a sample containing an analyte, produce a visualization species. Preferably, the visualization species is produced in proportion to the amount or concentration of the analyte. Analysis chemistry reagents preferably include a reactor and a substrate. The "reactor" is at least one compound, moiety and/or material; the "substrate" is also at least one compound, moiety and/or material. When the reactor and the substrate are mixed with the analyte, they will react to produce a visualization species. As used herein, the term "produce" includes forming by chemical reaction, as well as releasing from being bound or attached to something else. Preferably, the reactor is specific for an analyte, and the substrate is specific for a reactor. Preferably, the substrate includes a label. The reactor and the substrate may be attached, for example covalently or by hydrogen bonding (hybridization).

The term "visualization species" is a compound, moiety or material that can be detected, such as a fluorescent compound or a colored compound. A visualization species includes a label, which is that part of the visualization species that allows for detection, for example a colored label (such as a dye or a colored particle, including semiconductor nanoparticles (quantum dots)), a fluorescent label (such as fluorescent compound) or a magnetic label (such as a magnetic particle). Preferably, the label of the visualization species originated as the label of the substrate. It is possible for the visualization species and the substrate to be the same.

The term "specifically bind" means that binding between the two things is more favored binding, as compared to most other members of the same class or genus. For example, the binding between an antibody specific for an antigen, and the antigen; and hybridization between two complementary strands of DNA; are both examples of specific binding.

The term "aptamer" refers to nucleic acid that specifically binds a target compound or moiety. The term "nucleic acid enzyme" (NAE) refers to nucleic acid that catalyses a chemical reaction (such as cleavage of a substrate) when it binds a specific cofactor (such as a divalent metal ion). Both an aptamer and a nucleic acid enzyme are examples of reactors.

The term "conformational change" refers to the process by which a nucleic acid, such as an aptamer, adopts a different secondary or tertiary structure. The term "fold" may be substituted for conformational change.

DETAILED DESCRIPTION

The present invention makes use of the discovery of a compact reagent container for field use. The compact reagent container preferably includes analysis chemistry reagents, such as nucleic acid enzymes, which allow the device to be adapted to many different analytes. Concentrations of ions such as lead, uranium, copper, mercury, cadmium, silver, etc., may be detected as low as a part per billion (ppb) level. In addition, a nozzle, designed to accelerate a sample fluid through the compact reagent container, aids in mixing the sample fluid with the analysis chemistry reagents. When used with a standard fluorometer, the compact reagent container is capable of simply, rapidly, and inexpensively measuring very small concentrations of analytes.

Figure 1:
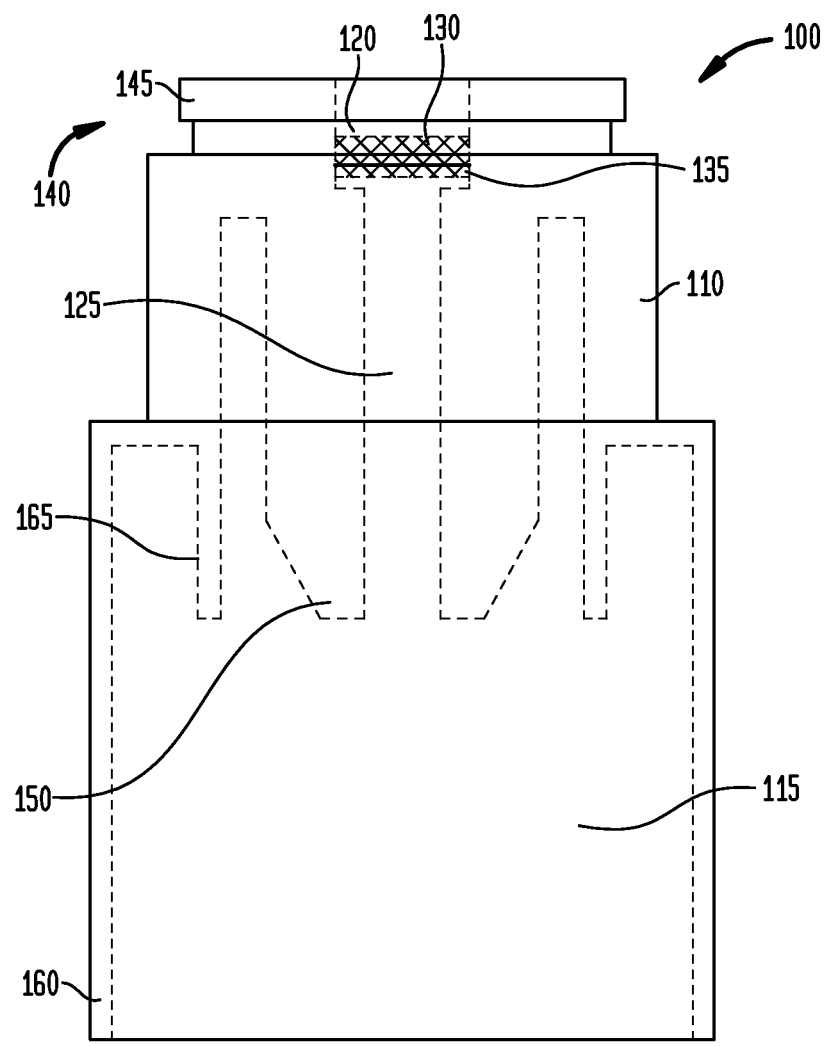
FIG. 1 illustrates an elevational view of a sensor base.

FIG. 1 illustrates an elevational view of a sensor base 100 having aspects of the present invention. The sensor base 100 includes an upper base body 110, a lower base body 115, a wide channel 120, a narrow channel 125, a frit 130, an insertive interlocking region 140, a nozzle 150, an outer skirt 160, and an inner skirt 165. The frit 130 includes dried reagents 135. The insertive interlocking region 140 includes a base baffle 145.

The upper base body 110 is disposed on the lower base body 115. The insertive interlocking region 140 is disposed on the upper base body 110. The base baffle 145 is disposed on the upper portion of the insertive interlocking region 140. The wide channel 120 is disposed in and extends axially through the center of the insertive interlocking region 140 and the upper base body 110. The narrow channel 125 is disposed below the wide channel 120 and is in fluid connection with the wide channel 120. The narrow channel 125 extends axially through the center of the upper base body 110, the lower base body 115, and the nozzle 150. The frit 130 is disposed in the wide channel 120. The dried reagents 135 are disposed on the frit 130. The outer skirt 160 forms the perimeter of the lower base body 115 and extends along the height of the lower base body 115. The inner skirt 165 is disposed within the outer skirt 160 and surrounds the nozzle 150.

In one aspect, the dimensions of the sensor base 100 are 15 mm×15 mm×22 mm. The lower base body 115 has a height of 14 mm. The upper base body 110 has a height of 6 mm and a diameter of 12 mm. The insertive interlocking region 140 has a height of 2 mm and a diameter of 9 mm. The base baffle 145 has a height of 1 mm. The wide channel 120 has a diameter of 4.5 mm. The narrow channel 125 has a diameter of 2 mm. Preferably, the cross-sectional area of the wide channel 120 at the frit 130 is greater than the cross-sectional area of the narrow channel 125 at the nozzle 150.

The frit 130 preferably contains dried reagents 135 such as analysis chemistry reagents. Such analysis chemistry reagents may include a nucleic acid or nucleic acid enzyme. Examples of useful analysis chemistry reagents can be found in U.S. Patent Application Publication, Pub. No. 2007/0269821, entitled "LATERAL FLOW DEVICES" to Mazumdar et al.; U.S. Pat. No. 6,706,474, entitled "NUCLEIC ACID ENZYME BIOSENSORS FOR IONS" to Lu et al.; U.S. Pat. No. 6,890,719, entitled "FLUORESCENCE BASED BIOSENSOR" to Lu et al.; International Publication Number WO 2009/012309, entitled "NUCLEIC ACID BASED FLUORESCENT SENSOR FOR COPPER DETECTION" to Lu et al.; International Publication Number WO 2009/045632, entitled "NUCLEIC ACID BASED FLUORESCENT SENSOR FOR MERCURY DETECTION" to Lu et al.; and U.S. Patent Application Publication, Pub. No. 2010/0151579, entitled "FLUORESCENT SENSOR FOR MERCURY" to Wang et al. The analysis chemistry reagents of these examples contain polynucleotides, such as nucleic acid enzymes, aptamers, aptazymes, and/or substrates; fluorophors; and quenchers. The visualization species and labels are fluorescent. U.S. Pat. No. 6,890,719 (noted above) describes analysis chemistry reagents including a nucleic acid enzyme and a substrate for the nucleic acid enzyme, each having a quencher, with one having a fluorophore. Other examples of useful analysis chemistry reagents are described in U.S. Patent Application Publication, Pub. No. 2006/0094026, entitled "NUCLEIC ACID ENZYME LIGHT-UP SENSOR UTILIZING INVASIVE DNA" to Lu et al.; and U.S. Patent Application Publication, Pub. No. 2007/0037171, entitled "APTAMER-BASED COLORIMETRIC SENSOR SYSTEMS" to Lu et al. These latter examples contain particles, and produce visualization species and labels that are colored. Alternatively, the visualization species and labels may be or a magnetic (such as a magnetic particle).

Preferably, the dried reagents 135 include one or more saccharides. The saccharide may be used to preserve the analysis chemistry reagents. The saccharide may be any water-soluble saccharide, including monosaccharides, disaccharides, and polysaccharides. Preferable monosaccharides may include mannose, fructose, or ribose. Preferable disaccharides may include trehalose, lactose, maltose, sucrose, or turanose. Preferable polysaccharides may include hydroxyethylstarch, inulin, or dextran. At present, a preferred saccharide is the disaccharide trehalose. Preferably, the amount of saccharide present in the dried reagent is 15 to 45% by weight, including 20, 25, 30, 35 and 40% by weight. Other chemicals may be present in the dried reagents, such as a buffer or salts. The dried reagent should be protected from contact with skin, and should be kept dry before use. The dried reagents may be prepared by mixing one or more sugars, the analysis chemistry reagents, optionally a buffer and optionally salts, and then allowing the mixture to air dry on the frit. Vacuum desiccation may then be used to further dry the dried reagents.

The frit typically comprises a porous material, such as a porous plastic media (e.g., polyethylene), or cellulose, having pore sizes in the range of 10-50 microns, in order to remove any particulates in the sample. The porous material of the frit may have a lower melting or degradation temperature than sensor base.

Figure 2:
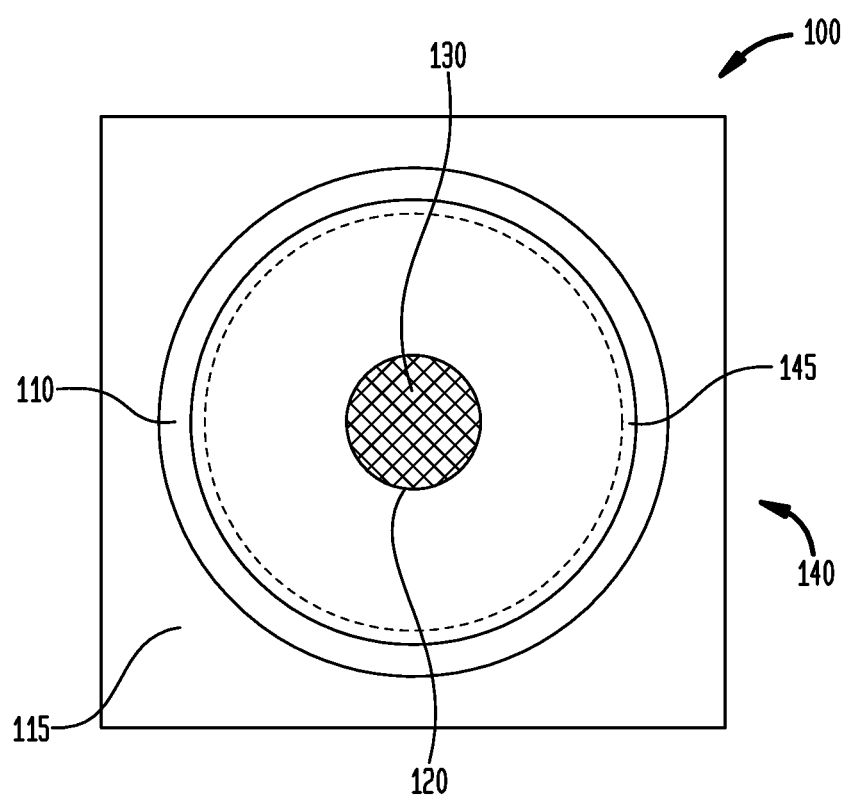
FIG. 2 illustrates a plan view of a sensor base.

FIG. 2 illustrates a plan view of a sensor base 100 having aspects of the present invention. The sensor base 100 includes an upper base body 110, a lower base body 115, a wide channel 120, a frit 130, and an insertive interlocking region 140. The insertive interlocking region 140 includes a base baffle 145.

Figure 3:
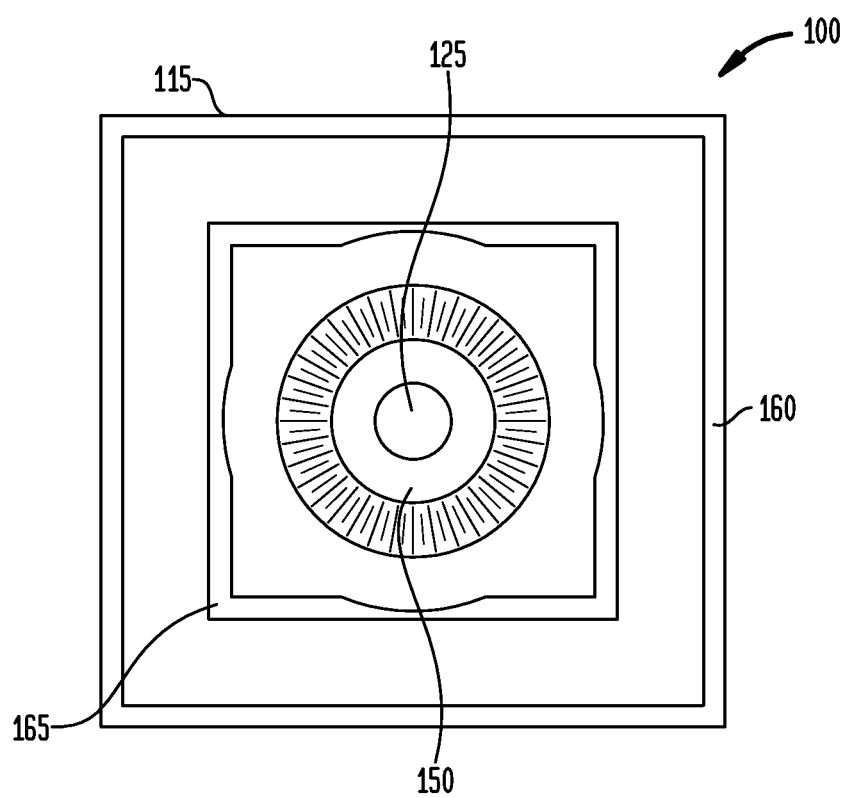
FIG. 3 illustrates an opposing view to FIG. 2 of a sensor base.

FIG. 3 illustrates an opposing view to FIG. 2 of a sensor base 100 having aspects of the present invention. The sensor base 100 includes a lower base body 115, a narrow channel 125, a nozzle 150, an outer skirt 160, and an inner skirt 165.

Figure 4:
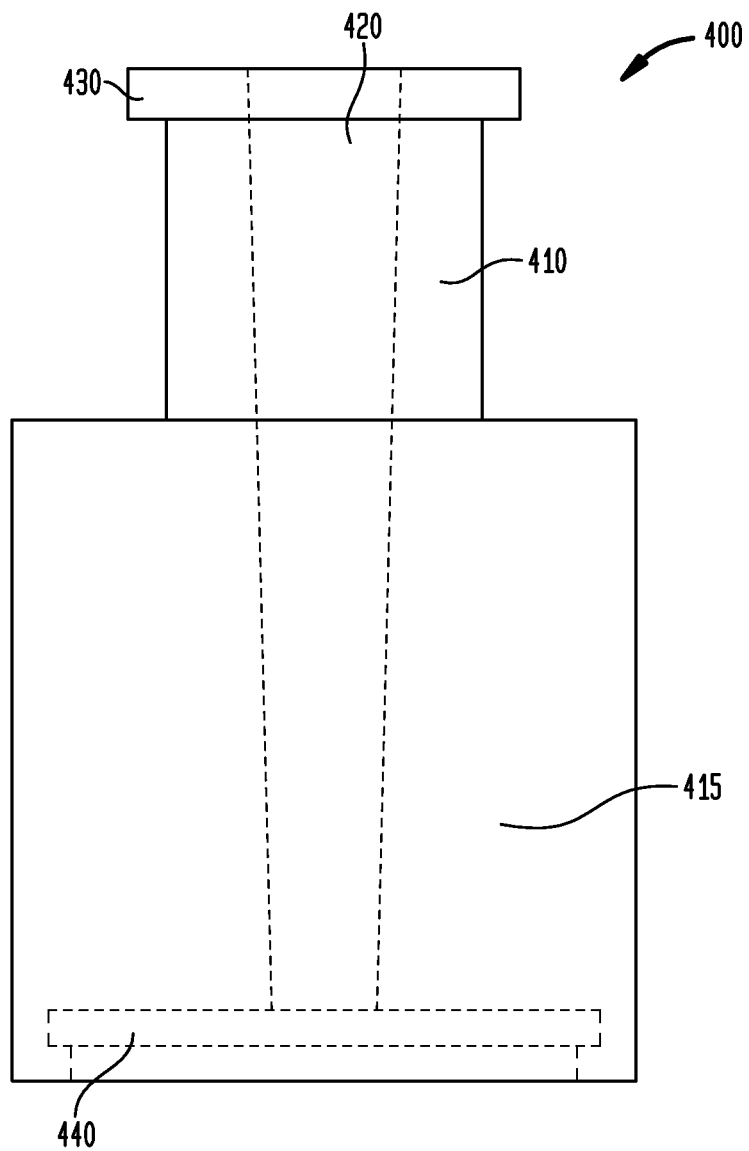
FIG. 4 illustrates an elevational view of a sensor cap.

FIG. 4 illustrates an elevational view of a sensor cap 400 having aspects of the present invention. The sensor cap 400 includes an upper cap body 410, a lower cap body 415, a cap channel 420, a cap baffle 430, and a receptive interlocking region 440.

The upper cap body 410 is disposed on the lower cap body 415. The cap baffle 430 is disposed on the upper portion of the upper cap body 410. The cap channel 420 is disposed in and extends axially through the center of the upper cap body 410 and the lower cap body 415. The diameter of the cap channel 420 decreases as it extends from the upper cap body 410 to the lower cap body 415. The receptive interlocking region 440 is disposed in the lower portion of the lower cap body 415.

Figure 5:
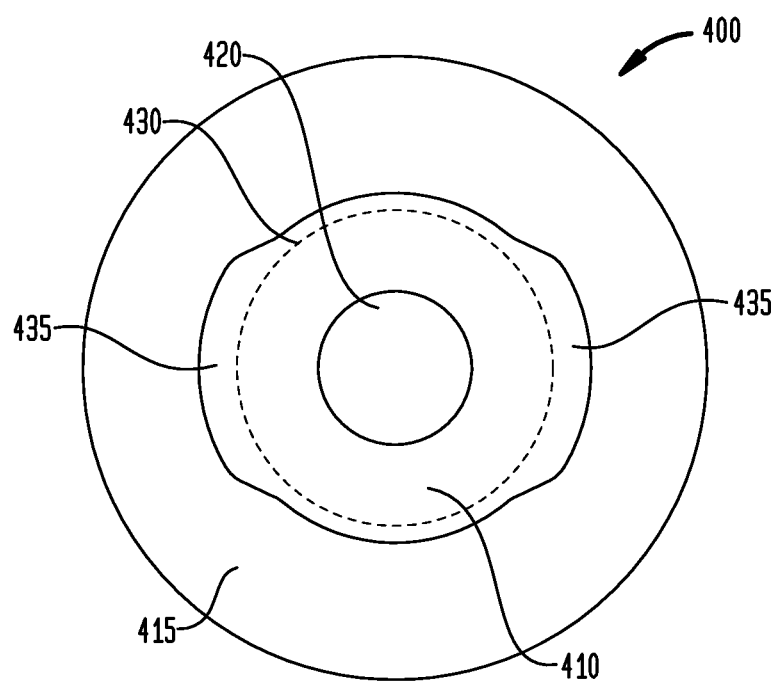
FIG. 5 illustrates a plan view of a sensor cap.

FIG. 5 illustrates a plan view of a sensor cap 400 having aspects of the present invention. The sensor cap 400 includes an upper cap body 410, a lower cap body 415, a cap channel 420, and a cap baffle 430. The cap baffle 430 includes baffle flares 435. The baffle flares 435 are disposed on opposing sides of the cap baffle 430.

Figure 6:
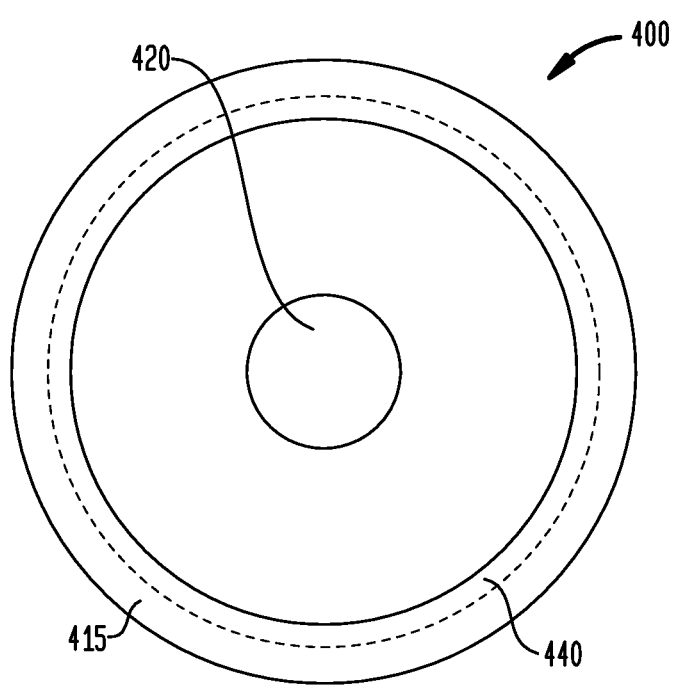
FIG. 6 illustrates an opposing view to FIG. 5 of a sensor cap.

FIG. 6 illustrates an opposing view to FIG. 5 of a sensor cap 400 having aspects of the present invention. The sensor cap 400 includes a lower cap body 415, a cap channel 420, and a receptive interlocking region 440.

In one aspect, the sensor cap 400 has a diameter of 12.5 mm and a height of 18 mm. The diameter of the cap baffle 430 is 6.5 mm. At the cap baffle 430, the diameter of the cap channel 420 is 4 mm. At the receptive interlocking region 440, the diameter of the cap channel 420 is 3 mm. The height of the lower cap body 415 is 12 mm, while the height of the upper cap body 410 is 6 mm. The diameter of the upper cap body 410 is 5.5 mm.

The sensor base 100 and sensor cap 400 preferably comprise a durable and inert polymeric material. Preferred polymeric materials include, for example, high-density polyethylene, low-density polyethylene, polypropylene, polycarbonate, polyethylene terephthalate, and polystyrene. Fabrication of the sensor base 100 and sensor cap 400 may be accomplished, for example, with injection molding.

Figure 7:
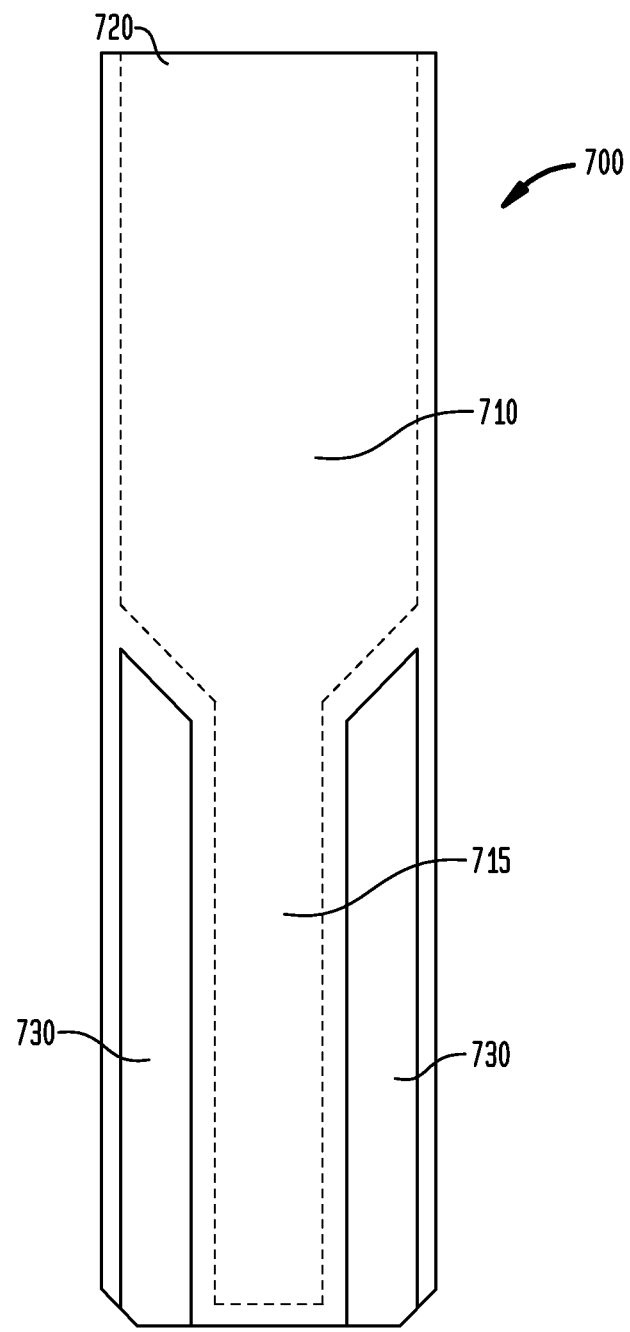
FIG. 7 illustrates an elevational view of a cuvette.

FIG. 7 illustrates an elevational view of a cuvette 700 for use with the present invention. The cuvette 700 includes an upper chamber 710, a lower chamber 715, cuvette opening 720, and orienting slots 730. The upper chamber 710 is fluidly connected to the lower chamber 715. The cuvette opening 720 is located at the upper portion of the upper chamber 710. The orienting slots 730 extend vertically along front and rear faces of the cuvette 700 and are located to the right and left of the lower chamber 715.

In operation, the cuvette 700 is inserted into a standard fluorometer. Preferably, the orienting slots 730 of the cuvette 700 fit a sample compartment of the fluorometer and prevent the cuvette 700 from being inserted into the fluorometer in an incorrect orientation.

In one aspect, the dimensions of the cuvette 700 are 45 mm×12 mm×12 mm. The width of the upper chamber 710 is 10 mm, while the width of the lower chamber 715 is 4 mm. The cuvette 700 preferably comprises a transparent material. Preferred materials include polycarbonate and glass. The cuvette 700 may be packaged and sold with the sensor base 100 and/or sensor cap 400, or it may be packaged and sold by itself in either individual or high quantity packaging.

Figure 8:
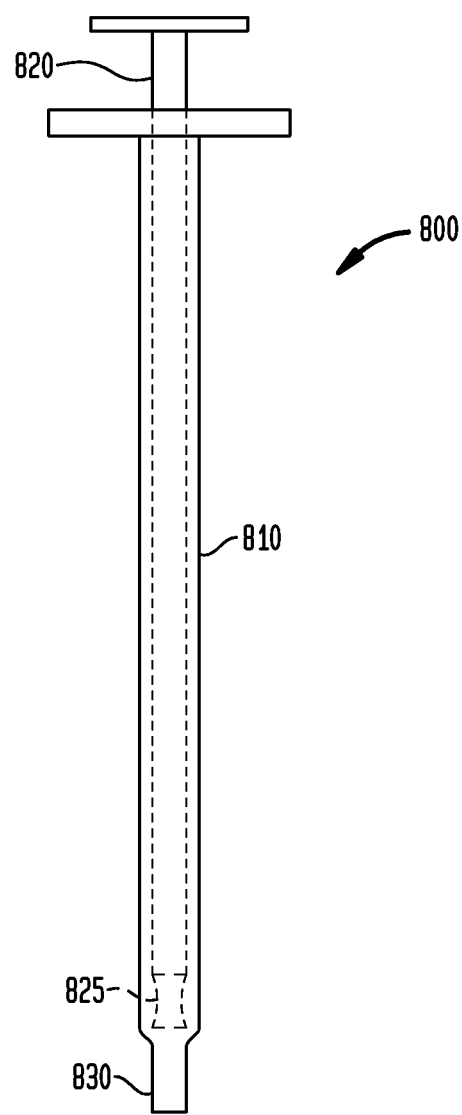
FIG. 8 illustrates a syringe.

FIG. 8 illustrates a syringe 800 for use with the present invention. The syringe 800 includes a barrel 810, a plunger 820, a rubber bulb 825, and a syringe tip 830. The rubber bulb 825 is coupled to the end of the plunger 820. The plunger 820 is slidably connected to the interior wall of the barrel 810 by the rubber bulb 825. The rubber bulb 825 forms a seal with the interior wall of the barrel 810. The syringe tip 830 is in fluid connection with the barrel 810.

In operation, the sensor cap 400 is placed on the sensor base 100. The insertive interlocking region 140 of the sensor base 100 is inserted into the receptive interlocking region 440 of the sensor cap 400, mechanically coupling the sensor cap 400 to the sensor base 100 to form a sensor housing 910, illustrated in FIG. 9. The base baffle 145 fits securely into the receptive interlocking region 440 of the sensor cap, decreasing the incidence of fluid leakage between the sensor cap 400 and the sensor base 100. The cuvette 700 is inserted into the lower base body 115 of the sensor base 100. Upon insertion of the cuvette 700, the outer skirt 160 of the sensor base 100 surrounds the perimeter of the upper chamber 710 of the cuvette 700, while the inner skirt 165 and the nozzle 150 of the sensor base 100 are disposed within the cuvette opening 720 of the upper chamber 710. When properly assembled, the sensor cap 400, sensor base 100, and cuvette 700 are in fluid connection.

A fluid sample is first collected by the syringe 800, typically about 1 ml. Depending upon the sample to be tested, additional sample conditioning or preparation may be used, such as using an EPA protocol to obtain a sample of lead paint, or adding a buffering agent to adjust pH, and/or salts, which may be provided in a sample tube or calibration tube. The syringe tip 830 is inserted into the cap channel 420 of the sensor cap 400. Preferably, the syringe tip 830 fits tightly into the cap channel 420 of the sensor cap 400 so as to decrease the incidence of fluid leakage. Once the plunger 820 of the syringe 800 is depressed, fluid travels through the cap channel 420 and into the wide channel 120 of the sensor base 100. As the fluid travels through the frit 130, it contacts and re-hydrates the dried reagents 135. The fluid sample and the re-hydrated reagents then flow into the narrow channel 125, out of the nozzle 150, through the upper chamber 710 of the cuvette 700, and into the lower chamber 715 of the cuvette 700. In conjunction with the cap channel 420, wide channel 120, and narrow channel 125, the nozzle 150 is designed to accelerate the sample fluid through the sensor housing 910 and into the cuvette 700. Such acceleration aids in mixing the sample fluid with the reagents. Once the reagents are mixed and reacting with the sample fluid in the upper chamber 710 and/or lower chamber 715 of the cuvette 700, the cuvette 700 can be inserted into and analyzed by a standard fluorometer. The cuvette 700 may be inserted into a standard fluorometer prior to filling with fluids.

Figure 9:
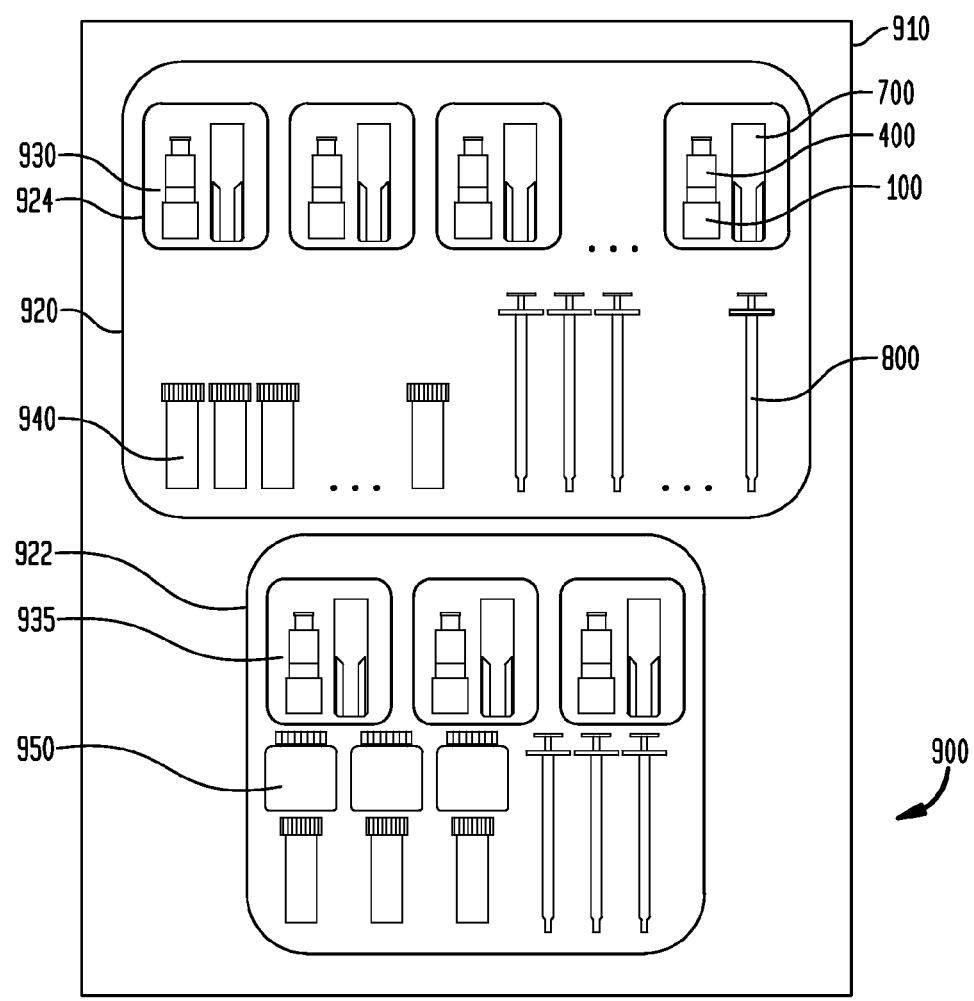
FIG. 9 illustrates a bag which contains a plurality of sensor housings.

FIG. 9 illustrates a kit 900 having aspects of the present invention. The kit 900 includes a box 910, which contains a first bag 920 and a second bag 922. The first bag 920 contains a plurality of black bags 924, a plurality of sample tubes 940, and a plurality of syringes 800. Each black bag 924 in the first bag 920 contains a sensor housing 930, a cuvette 700, and a desiccant (not shown in FIG. 9). Each sensor housing 930 includes a sensor base 100 and a sensor cap 400. The second bag 922 contains three black bags 924, three sample tubes 940, three calibration tubes 950, and three syringes 800. Each black bag 924 in the second bag 922 contains a calibration sensor 935, a cuvette 700, and a desiccant (not shown in FIG. 9). The calibration sensor 935 includes a sensor base 100 and a sensor cap 400. Preferably, each black bag 924 blocks light from impinging upon the sensor housings 930 and/or calibration sensors 935.

The calibration sensor 935 may be provided with a calibration tube 950, which may containing a buffer and a known amount of the analyte of interest, for example lead with a buffer for pH 7, or $UO_2^{2+}$ with a buffer for pH 5, and is used to calibrate a fluorometer. A sample tube 940 may be provided with each sensor housing 930, and also may contain a buffer. Other agents that may also be provided in the calibration and/or sample tube include salts, and organic chelators. The reagents present in the sample tube and/or calibration tube may be present in liquid form as a solution, or as a dry pellet or powders. The dried reagent on the frit of the calibration sensor 935 may also include additional buffer to compensate for acidity of the calibration amount of analyte. Examples of biological buffers include MES, HEPES, Tris, MOPS etc., and examples of salts include sodium chloride, potassium chloride, ammonium chloride, magnesium chloride, calcium chloride etc. A calibration standard could also be provided as a solution in a bottle, or in an ampoule.

The sensor housings 930 may be sold and/or distributed in bulk. For example, a plurality of sensor housings 930 may be distributed in bags which contain twenty-five, fifty, or one hundred sensor housings 930. Alternatively, the sensor bases 100 and sensor caps 400 of the sensor housings 930 may be distributed separately. The sensor base and the sensor cap may be snapped together, or ultrasonically welded together, to help minimize any leakage.

An example of a kit is a box, containing sensor housings, calibration sensor housing, syringes, sample tubes, calibration tubes, and cuvettes. The sensor housings may each be packaged in a bag, such as a black bag that keeps out light, along with a cuvette, and a desiccant. The calibration sensor housings may each be packaged in a bag, such as a black bag that keeps out light, along with a cuvette, and a desiccant. The bags of calibration sensor housing may be packed into a larger bag, which contain calibration tubes and syringes for use with the calibration sensors. The bags of sensor housing may similarly be packed into a larger bag, which contains sample tubes and syringes for use with the sensors. The calibration and sample tubes may be 5 ml or 20 ml tubes, for example.

The sensor housings 930 may be color-coded to signify the analyte which they are capable of detecting. In an exemplary embodiment, sensor housings 930 are color-coded to correspond to selected analytes, such as green for lead, orange for uranium, blue for copper, etc., with darker or lighter corresponding colors utilized for the sensor housings 930 used in the corresponding calibration of the selected analyte. Preferably, the calibration sensor 935 for a particular analyte is colored a different shade than the sensor housings 930.

EXAMPLE

The following is an example of using a sensor housing:
Open the black bag which contains sensor in green plastic housing and plastic cuvette for lead analysis. The bag contains a transparent desiccant pouch which should be discarded. Place the plastic cuvette in the instrument, and then place the sensor housing on the cuvette. Collect test water in a clean cup, then slowly pour the test water into the provided sample tube containing liquid buffer up to the 5 mL mark. Close the cap tightly and mix well by shaking Next, draw 1 ml of water from the sample tube into a syringe. Attach the syringe to the housing over the cuvette in the instrument. Squeeze water through housing into the cuvette, then quickly remove the housing and syringe, close the sample chamber door of the instrument.

What is claimed is:

1. A sensor for use with a cuvette, the sensor comprising:
a porous substrate having an analysis chemistry reagent; and
a sensor housing comprising a sensor cap and a sensor base, wherein:
the sensor cap comprises:
a first channel; and
a first interlocking region, the first channel having a first diameter at the first interlocking region; and
the sensor base comprises:
a second interlocking region to mate with the first interlocking region;
a second channel adjacent the second interlocking region, the second channel holding the porous substrate and in fluid communication with the first channel, the second channel having a second diameter greater than the first diameter;
a third channel coupled to and in fluid communication with the second channel, the third channel having a third diameter smaller than both the first diameter and the second diameter; and,
an outer housing wall to fit over and around a perimeter of an upper chamber of the cuvette.

2. The sensor of claim 1, wherein the sensor base further comprises:
a nozzle, in fluid connection with the third channel and insertable into an opening of the cuvette to direct liquid flow into a lower chamber of the cuvette.

3. The sensor of claim 2, wherein the sensor base further comprises:
an inner housing wall coupled to and spaced apart from the nozzle and the outer housing wall, the inner housing wall to fit within the upper chamber of the cuvette.

4. The sensor of claim 1, wherein the coupling of the third channel and the second channel form a second channel base, and the porous substrate is held in between a lower surface of the sensor cap at the first interlocking region and the second channel base, and further in contact with the third channel.

5. The sensor of claim 1, wherein the first diameter of the first channel at the first interlocking region is substantially at least about 1.5 times the third diameter of the third channel at the porous substrate and the second diameter of the second channel is substantially at least about 2.0 times the third diameter at the porous substrate.

6. The sensor of claim 1, wherein the porous substrate is a frit and the analysis chemistry reagent comprises a nucleic acid enzyme and a fluorophore.

7. The sensor of claim 1, wherein:
the sensor cap further comprises a sensor cap baffle and baffle flares disposed on opposing sides of the sensor cap baffle; and
wherein the first channel extends axially through the sensor cap, the second and third channels extend axially through the sensor base, and an upper portion of the first channel of the sensor cap is to receive and removably couple tightly to a syringe having a sample for injection of the sample into the sensor housing.

8. The sensor of claim 1, wherein the sensor housing is color-coded using a plurality of colors, each color of the plurality of colors to signify a selected analyte for detection in a sample or in a calibration sample.

9. The sensor of claim 1, wherein the first interlocking region is a receptive interlocking region and the second interlocking region is an insertive interlocking region.

10. The sensor of claim 1, wherein the sensor cap and the sensor base have been snapped or welded together.

11. A sensor for use with a cuvette, the sensor comprising:
a sensor housing comprising a sensor cap and a sensor base, wherein:
the sensor cap comprises:
a first axial channel; and
a first interlocking region, the first axial channel having a first diameter at the first interlocking region; and
the sensor base comprises:

a second interlocking region to mate with the first interlocking region;

a second axial channel adjacent the second interlocking region, the second axial channel holding the porous substrate and in fluid communication with the first axial channel, the second axial channel having a second diameter greater than the first diameter;

a third axial channel coupled to the second axial channel to form a lower rim in the second axial channel and in fluid communication with the second axial channel, the third axial channel having a third diameter smaller than both the first diameter and the second diameter;

a nozzle, in fluid connection with the third channel and insertable into an opening of the cuvette to direct liquid flow into a lower chamber of the cuvette;

an outer housing wall to fit over and around a perimeter of an upper chamber of the cuvette; and an inner housing wall coupled to and spaced apart from the nozzle and the outer housing wall, the inner housing wall to fit within the upper chamber of the cuvette;

and a porous substrate held in the second axial channel between a lower surface of the sensor cap at the first interlocking region and the lower rim of the second axial channel of the sensor base and in fluid communication with the first and third axial channels, the porous substrate having an analysis chemistry reagent.

12. The sensor of claim 11, wherein the coupling of the third axial channel and the second axial channel form a second channel base, and the porous substrate is held in between a lower surface of the sensor cap at the first interlocking region and the second channel base, and further in contact with the third axial channel.

13. The sensor of claim 11, wherein the first diameter of the first axial channel at the first interlocking region is substantially at least about 1.5 times the third diameter of the third axial channel at the porous substrate and the second diameter of the second axial channel is substantially at least about 2.0 times the third diameter at the porous substrate.

14. The sensor of claim 11, wherein the porous substrate is a frit and the analysis chemistry reagent comprises a nucleic acid enzyme, a fluorophore, and a saccharide.

15. The sensor of claim 11, wherein:

the sensor cap further comprises a sensor cap baffle and baffle flares disposed on opposing sides of the sensor cap baffle; and wherein an upper portion of the first axial channel of the sensor cap is to receive and removably couple tightly to a syringe having a sample for injection of the sample into the sensor housing.

16. The sensor of claim 11, wherein the sensor housing is color-coded using a plurality of colors, each color of the plurality of colors to signify a selected analyte for detection in a sample or in a calibration sample.

17. A sensor for use with a cuvette, the sensor comprising:

a porous substrate having an analysis chemistry reagent, the analysis chemistry reagent comprising a nucleic acid enzyme, a fluorophore, and a saccharide; and a sensor housing comprising: a sensor cap and a sensor base, wherein:

the sensor cap comprises:

a first axial channel, an upper portion of the first axial channel removably coupleable to a syringe having a sample for injection of the sample into the sensor housing: and a first interlocking region, the first axial channel having a first diameter at the first interlocking region;

a sensor cap baffle; and baffle flares disposed on opposing sides of the sensor cap baffle the sensor base comprises:

a second interlocking region to mate with the first interlocking region;

a second axial channel adjacent the second interlocking region, the second axial channel holding the porous substrate and in fluid communication with the first axial channel, the second channel having a second diameter greater than the first diameter;

a third axial channel coupled to and in fluid communication with the second axial channel, the third axial channel having a third diameter smaller than both the first diameter and the second diameter;

a nozzle, in fluid connection with the third axial channel and insertable into an opening of the cuvette to direct liquid flow into a lower chamber of the cuvette;

an outer housing wall to fit over and around a perimeter of an upper chamber of the cuvette; and an inner housing wall coupled to and spaced apart from the nozzle and the outer housing wall, the inner housing wall to fit within the upper chamber of the cuvette; and wherein the porous substrate is held in the second axial channel between a lower surface of the sensor cap at the first interlocking region and a lower rim of the second axial channel of the sensor base and in fluid communication with the first and third axial channels; and wherein the sensor housing is color-coded using a plurality of colors, each color of the plurality of colors to signify a selected analyte for detection in a sample or in a calibration sample.

* * * * *